United States Patent [19]

Stierstorfer

[11] Patent Number: 5,737,382
[45] Date of Patent: Apr. 7, 1998

[54] X-RAY COMPUTED TOMOGRAPHY APPARATUS WITH OPTIMIZED READOUT OF A PLANAR X-RAY DETECTOR

[75] Inventor: Karl Stierstorfer, Erlangen, Germany

[73] Assignee: Siemens Aktiengesellschaft, Munich, Germany

[21] Appl. No.: 754,035

[22] Filed: Dec. 3, 1996

[30] Foreign Application Priority Data

Jan. 3, 1996 [DE] Germany ............... 196 00 115.3

[51] Int. Cl.[6] ............................................. A61B 6/03
[52] U.S. Cl. ................................................ 378/19; 378/4
[58] Field of Search ........................... 378/4, 19, 98.8

[56] References Cited

U.S. PATENT DOCUMENTS 5,355,309 10/1994 Eberhardd et al. .
5,430,784 7/1995 Ribner et al. ........................ 378/19
5,570,403 10/1996 Yamazaki et al. ................ 378/19 X
5,625,661 4/1997 Oikawa .............................. 378/19 X

FOREIGN PATENT DOCUMENTS

OS 195 15
778        11/1995  Germany .
6-296607   10/1994  Japan ............................... 378/19

*Primary Examiner*—David P. Porta
*Attorney, Agent, or Firm*—Hill, Steadman & Simpson

[57] ABSTRACT

In an X-ray computed tomography apparatus with a planar detector an optimum readout of the detector elements ensues by forming the planar detector of a number of sub-detectors. Each sub-detector is composed of a matrix of detector elements. A simultaneous readout of one detector element from each of the sub-detectors ensues.

3 Claims, 3 Drawing Sheets

X-RAY COMPUTED TOMOGRAPHY APPARATUS WITH OPTIMIZED READOUT OF A PLANAR X-RAY DETECTOR

BACKGROUND OF THE INVENTION

1. Field of the Invention

The present invention is directed to an X-ray computed tomography apparatus of the type having a planar X-ray detector.

2. Description of the Prior Art

The tube power represents a significant limitation in X-ray computed tomography. The reason is that only a narrow fan beam is gated out from the overall ray cone and used. If an existing dose could be better exploited, a given volume could be registered in a shorter time or a larger volume could be registered in a given time (for example, while the patient is holding his breath). In order to achieve a better utilization of the tube dose, the detector (planar detector) must be stretched in the direction of the system axis (z-direction). So that the resolution in z-direction is not deteriorated, the detector must be divided into a number of parallel lines in the z-direction, each line composed of a row of detector elements. The information is integrated during a system clock pulse in every detector element and is subsequently read out. As a consequence of the large number (M*N) of detector elements, this cannot occur simultaneously (or nearly simultaneously) for all elements. The readout must thus ensue in a partially sequential way. The sequential signals are then supplied to a number of amplifiers and then to an A/D converter.

SUMMARY OF THE INVENTION

An object of the present invention is to optimize an X-ray computed tomography apparatus with a planar detector with respect to the readout of the information of the detector elements.

The above is achieved in accordance with the principles of the present invention in a computed tomography apparatus having a planar X-ray detector composed of a number of sub-detectors arranged in a row, with each sub-detector being constructed of a matrix of detector elements, with readout of the planar detector being controlled so that one detector element is simultaneously read out from each sub-detector. The readout continues in this manner until all detector elements from each of the sub-detectors have been read out.

DESCRIPTION OF THE PREFERRED EMBODIMENTS

Figure 1:
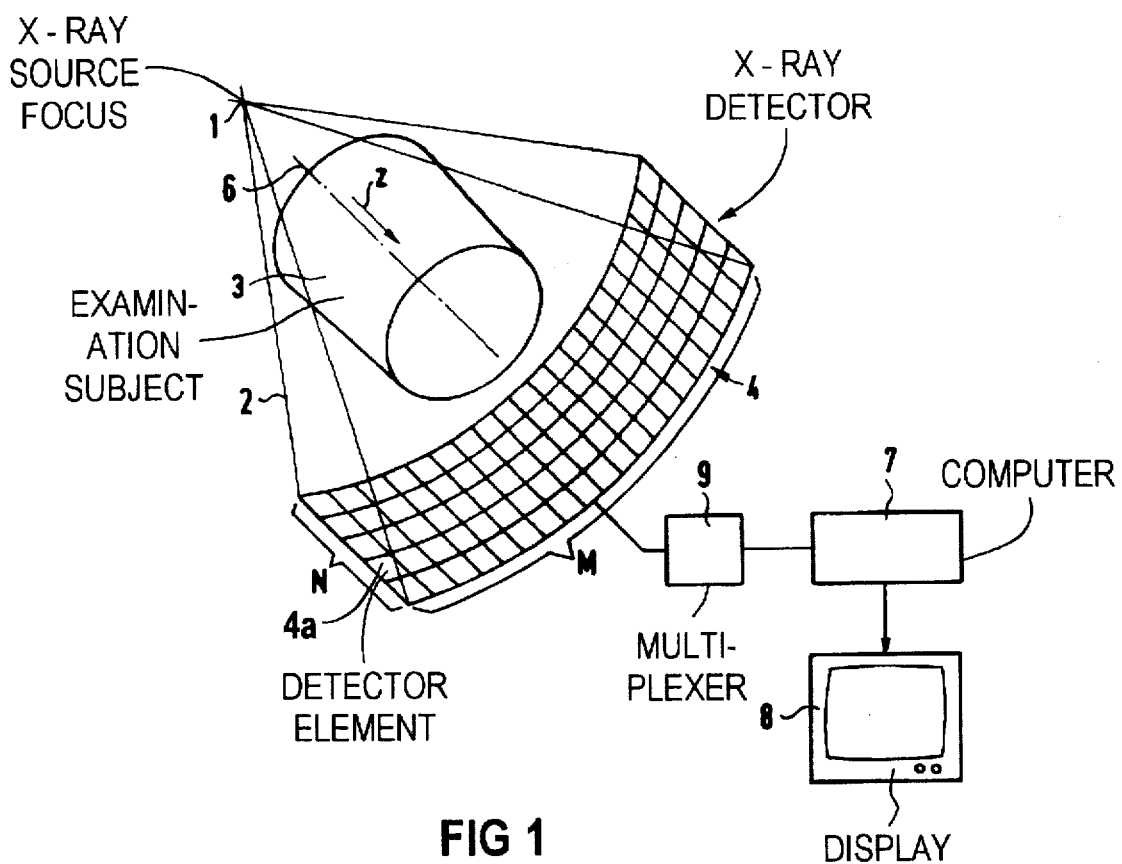
FIG. 1 shows an X-ray computed tomography apparatus with a planar detector for explaining the basis of the invention.

FIG. 1 shows the focus 1 of an X-radiator from which a pyramidal X-ray beam 2 gated by a diaphragm (not shown) emanates. This X-ray beam 2 penetrates a subject 3 and is incident on a detector 4 that is composed of a number of parallel detector lines, each of which is formed by a row of detector elements. The measuring system composed of the X-radiator with the focus 1 and the detector 4 is rotatable around a system axis 6, so that the subject 3 is transirradiated from different projection directions. A computer 7 calculates an image of the subject 3 from the detector signals thereby formed, this image being reproduced on a monitor 8. The acquisition of the detector signals ensues with a multiplexer 9.

Figure 2:
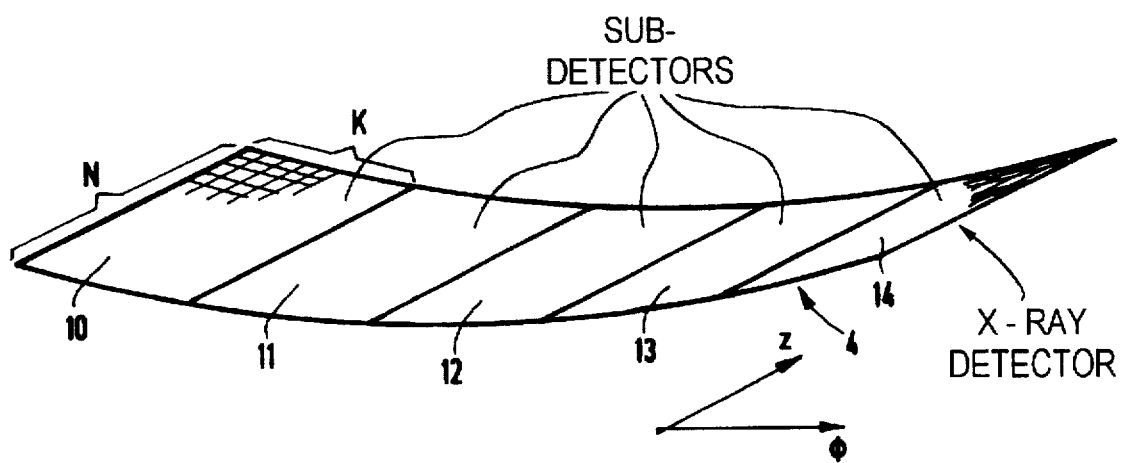
FIG. 2 is an illustration of the planar detector in the computed tomography apparatus of FIG 1.

FIG. 2 shows that the detector 4 is composed of a number of sub-detectors 10 through 14. Each sub-detector 10 through 14 is composed of a matrix with K*N detector elements.

Figure 3:
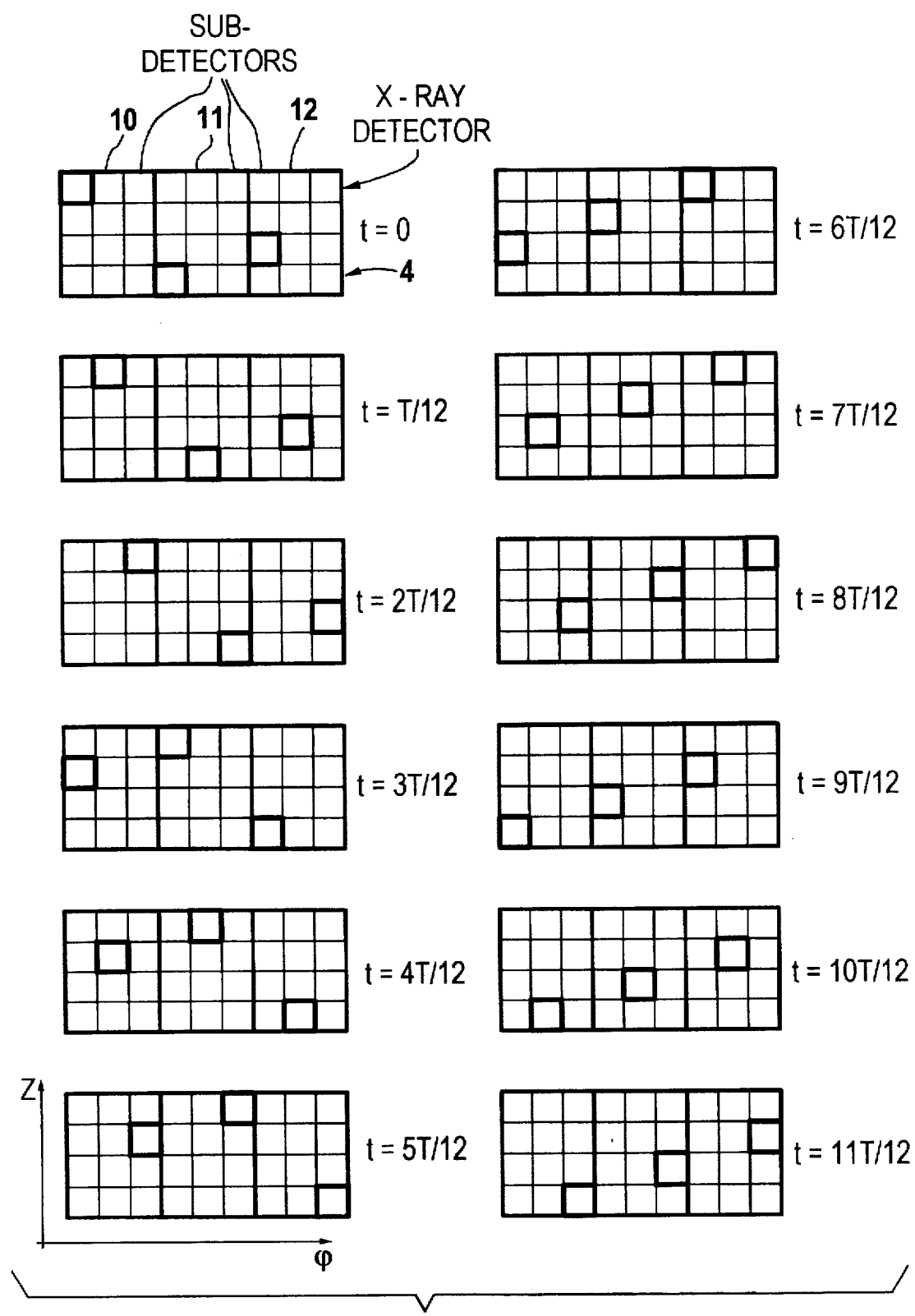
FIG. 3 illustrates a first version for readout of the planar detector of FIGS. 1 and 2.

FIG. 3 shows the readout pattern for M=9, K=3, N=4. M is the number of detector elements per line. The detector element respectively read out is shown with a heavy outline. These outlined detector elements are read out at the respectively indicated time. According to FIG. 3, the readout ensues zig-zag.

The elements are read out column-by-column. The readout cycles of neighboring elements must be offset by T/N so that the time intervals between the readouts of horizontally neighboring elements are constant over the boundaries of the sub-detectors 10, etc. Horizontally neighboring elements are read out offset by the time T/(K*N); vertically neighboring elements are read out offset by the time T/N.

Figure 4:
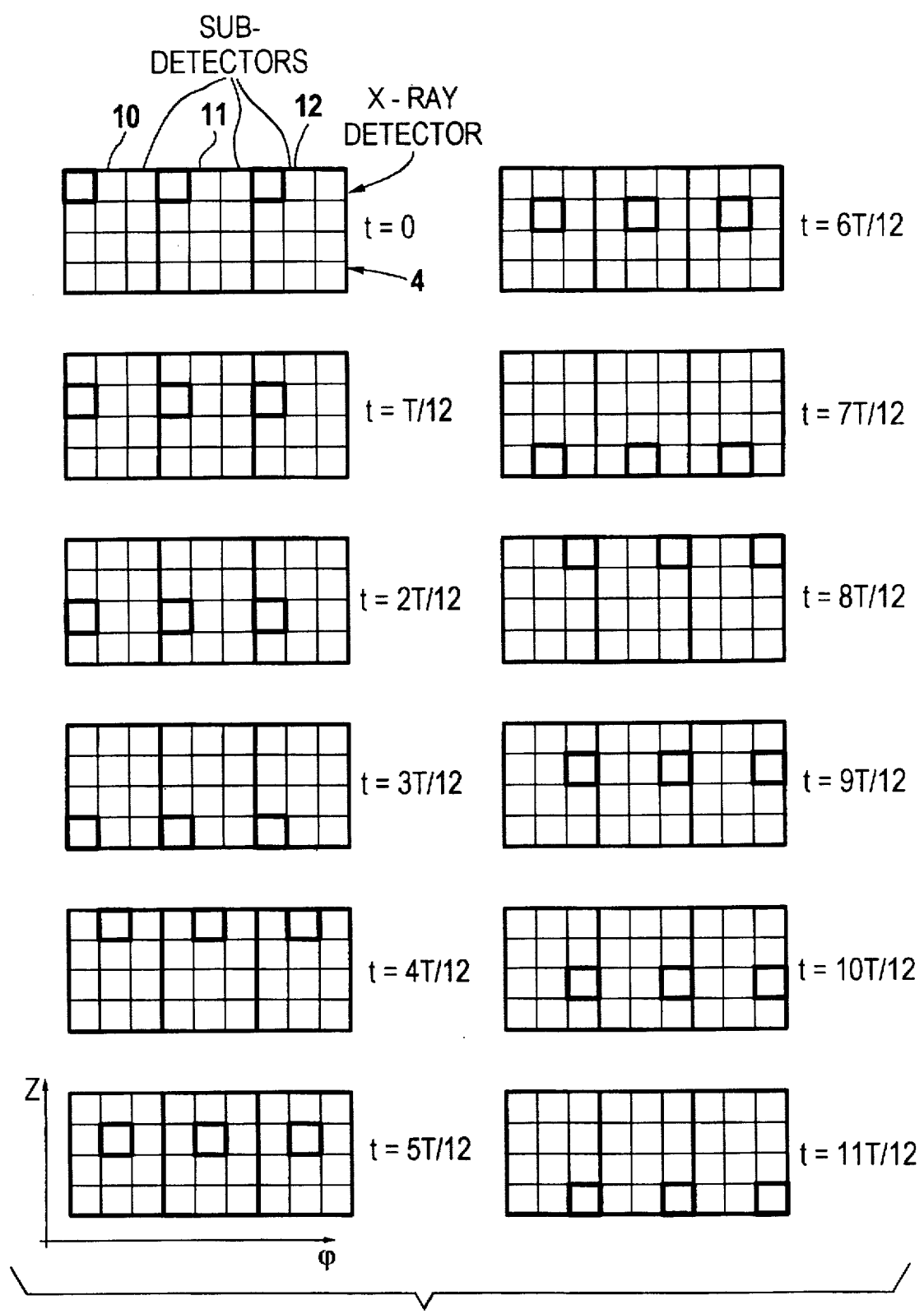
FIG. 4 illustrates a second version for readout of the planar detector of FIGS. 1 and 2.

FIG. 4 shows a readout pattern for the case M=9, K=3, N=4, whereby the bounded detector elements are respectively read out at the indicated time and the readout ensues row-by-row and column-by-column. A time offset between the readout of the sub-detectors is not necessary. Horizontally neighboring elements are read out offset by the time T/K; vertically neighboring elements are read out offset by the time T/(K*N).

It is also possible to equip parts of a sub-detector with respective signal converter chains. Both patterns can then be applied to these sub-divisions. K and N are then the dimensions of the sub-division.

FIG. 4 shows that respective detector elements corresponding to one another, i.e. detector elements that reside at the same location of the matrix, can be simultaneously read out from each of the sub-detectors 10, etc.

Although modifications and changes may be suggested by those skilled in the art, it is the intention of the inventors to embody within the patent warranted hereon all changes and modifications as reasonably and property come within the scope of their contribution to the art.

We claim as our invention:

1. An X-ray computed tomography apparatus comprising:
   means for scanning an examinations subject from a plurality of successive projection directions proceeding along a rotational direction, including an X-ray source and a planar X-ray detector;
   said planar X-ray detector comprising a plurality of sub-detectors disposed successively in a sequence in a row proceeding along said rotational direction, each sub-detector comprising a plurality of detector elements arranged in a matrix; and
   means for controlling readout of said X-ray detector for simultaneously reading out only one detector element from each of said sub-detectors proceeding along said rotational direction until all detector elements in all of said sub-detectors have been read out.

2. An X-ray computed tomography apparatus as claimed in claim 1 wherein said means for controlling readout of said X-ray detector comprises means for successively reading out the detector elements in each matrix in a zig-zag sequence proceeding along said rotational direction.

3. An X-ray computed tomography apparatus as claimed in claim 1 wherein said matrixes respectively have detector elements in respective positions corresponding to the positions of the detector elements in the other matrixes, and wherein said means for controlling readout of said X-ray detector comprise means for simultaneously reading out corresponding detector elements.

* * * * *